US008538775B2

(12) United States Patent
Skomra

(10) Patent No.: US 8,538,775 B2
(45) Date of Patent: Sep. 17, 2013

(54) MOBILE WIRELESS MEDICATION MANAGEMENT SYSTEM

(75) Inventor: Stewart Alan Skomra, Poway, CA (US)

(73) Assignee: QUALCOMM Incorporated, San Diego, CA (US)

( * ) Notice: Subject to any disclaimer, the term of this patent is extended or adjusted under 35 U.S.C. 154(b) by 1348 days.

(21) Appl. No.: 11/839,723

(22) Filed: Aug. 16, 2007

(65) Prior Publication Data

US 2009/0048871 A1    Feb. 19, 2009

(51) Int. Cl.
*G06Q 10/00* (2012.01)

(52) U.S. Cl.
USPC .................................. 705/3; 705/2

(58) Field of Classification Search
USPC .......................................................... 705/3
See application file for complete search history.

(56) References Cited

U.S. PATENT DOCUMENTS

| 5,502,944 | A | * | 4/1996 | Kraft et al. | 53/55 |
|---|---|---|---|---|---|
| 6,161,095 | A | * | 12/2000 | Brown | 705/2 |
| H2120 | H | * | 7/2005 | Cudlitz | 235/382 |
| 6,985,870 | B2 | * | 1/2006 | Martucci et al. | 705/3 |
| 7,154,397 | B2 | * | 12/2006 | Zerhusen et al. | 340/573.1 |
| 2004/0121767 | A1 | * | 6/2004 | Simpson et al. | 455/426.1 |
| 2007/0226511 | A1 | * | 9/2007 | Wei et al. | 713/186 |

FOREIGN PATENT DOCUMENTS

| CN | 1759398 | A | 4/2006 |
|---|---|---|---|
| EP | 1355252 | A1 | 10/2003 |
| JP | 2001312566 | A | 11/2001 |
| JP | 2004157579 | A | 6/2004 |
| JP | 2004167158 | A | 6/2004 |
| JP | 2005062994 | | 3/2005 |
| JP | 2005334056 | A | 12/2005 |
| JP | 2006268585 | A | 10/2006 |
| WO | WO03014871 | A2 | 2/2003 |

OTHER PUBLICATIONS

International Search Report and Written Opinion—PCT/US2008/073383, International Searching Authority—European Patent Office, Jun. 19, 2009.

* cited by examiner

*Primary Examiner* — Michael Fuelling
(74) *Attorney, Agent, or Firm* — James T. Hagler

(57) ABSTRACT

The specification and drawing figures describe and show a system for medication management is disclosed, illustrated, and claimed that includes a mobile wireless communication instrument. A data processing system (100) housed in the portable wireless communications instrument is included to receive, store, and transmit images and data. A programmable medication management protocol is stored in memory (104) of the data processing system (100) to image-identify and image-authenticate components of the medication management protocol. A notification subsystem is included to either confirm or reject use of the medication.

12 Claims, 2 Drawing Sheets

MOBILE WIRELESS MEDICATION MANAGEMENT SYSTEM

BACKGROUND

1. Field

The apparatus, system, and method described, illustrated, and claimed in this document relate generally to a mobile wireless communications instrument capable of implementing a medication management system. More specifically, the mobile wireless medication management system uses a protocol that may be stored in memory in a computer processor or data processor that is operatively connected to the mobile wireless communications instrument to implement the medication management requirements of the protocol. The use of the mobile wireless communications instrument in combination with the protocol allows a patient and a medication provider, to confirm use and/or ingestion by the patient of a correct medication prescription, at the correct time, in the correct dosages. A notification subsystem is included to either confirm or reject use of the medication.

2. Background

As the U.S. Food and Drug Administration warned in an article entitled "Medical Errors Can Be Deadly Serious," the Institute of Medicine of the National Academy of Sciences reported that between 44,000 and 98,000 Americans die each year not from the medical conditions they sought help for, but from preventable medical errors. A "medical error" may include a health-care provider choosing an inappropriate method of care; or intending to infuse a patient with one medicine, but inadvertently giving the patient another medicine or a different dosage. As a result, such medical errors are the eighth leading cause of death among Americans. Indeed, medical errors exceed those from motor vehicle accidents (43,458), breast cancer (42,297), and A/DS (16,516). Patients in hospitals are only a small proportion of those at risk, according to studies made by the FDA, because doctor's offices, clinics, and outpatient surgical centers treat thousands of patients daily. In addition, retail pharmacies fill countless prescriptions. Nursing homes and other institutional venues serve a vulnerable patient population.

What the FDA report described as the seemingly simple process of giving a patient medicine—the right drug, in the right dose, to the right patient, at the right time—is, in reality, teeming with opportunities for error. Confusion and medication mismanagement often seem symbiotic.

The confusion arises from sound-alike names; from look-alike containers having look-alike labels patients rarely pause to read; and from a patient having the correct drug in the correct dosage, but selecting the incorrect medicine from among a variety of medicines the patient uses.

As of July 2005, one publication reported that the annual cost of drug-related morbidity and mortality was nearly $177 billion in the United States. Medication errors had occurred in about one of every five: doses given in hospitals. The report quoted the FDA in stating that there is at least one death per day, and 1.3 million people injured each year, due to medication mismanagement.

The problem of incorrect medication ingestion and use is not limited to the United States. Similar reports emanate from abroad. For example, a report from the United Kingdom in late 2004 indicated that drug prescription errors were a common cause of adverse incidents although largely preventable. A similar report was published in Australia.

Interest in the use of data processors and, by implication, mobile wireless communications instruments to help manage medication prescription and use, already is evident. But for the fear of loss of privacy and theft of the database, posting medical records of patients online for availability at least in event of emergency would be already a reality.

Based on a report entitled "Caremark: Clinical Up-Date," from the office of the U.S. Inspector General, August 2001, annual costs to the health care industry of failure to provide the right medication in the right dosages at the right time is staggering. The estimates then of the cost included $100 billion to health care payers; 125,000 deaths per year due to heart attack and strokes; $30 billion lost sales to pharmaceutical companies; $8 billion in lost revenue for pharmacies; and add-on costs $31.3 billion, or 23% of all nursing home admissions for the additional costs associated with using bar codes and/or RFD tags.

It is apparent, therefore, that a medication management system not only is useful, but necessary. While the mobile wireless medication management system disclosed, illustrated, and claimed in this document could be enabled using a variety of devices and apparatus, use of a mobile wireless communications instrument as at least one of the preferred devices or apparatus is appropriate in view of the national and international exponential increase in use of mobile wireless communications instruments by people of all ages and genders. Many mobile wireless communications instruments now are adapted to create and transmit images across a mobile wireless communications system, a capability that assists in implementing the medication management system. Of course, use of a mobile wireless communications instrument is not a limitation of the invention of this document. The mobile wireless medication management system may be implemented using a variety of wireless and non-wireless apparatus and devices.

Alternatives to the present invention have been suggested. One alternative is generally referred to as an RFID system. Radio-frequency identification ("RFID)" is an automatic identification method relying on storing and remotely retrieving data using devices called RFID tags or transponders. An RFID tag can be attached to or incorporated into a product, animal, or person for purpose of identification using radio waves. All RFID tags contain at least two parts, an integrated circuit for storing and processing information, modulating and demodulating a radio frequency ("RF") signal, and perhaps other specialized functions; and an antenna for receiving and transmitting the signal.

Because medicines, including pills and fluids, are often required to be strictly accounted for, the use of RFID in the medical field has been explored. However, RFID is a comparatively expensive solution to medication management problems. Another limitation is the read distance range of some forms of RFID tags, which may be only four inches. Another limitation of RFD)'s is the need for an external antenna significantly larger than the chip in the best version thus far developed. The cost of implementing an RFID program, however, remains the principle limitation.

Recently the U.S. Food and Drug Administration issued a ruling that essentially begins a final review process that will determine whether hospitals may use RFID systems to identify patients and/or permit relevant hospital staff to access medical records. Since then, a number of U.S. hospitals have begun implanting patients with RFID tags and using RFID for inventory management. As will be evident to those skilled in the art, it is much less invasive to use the system for medicine management described, illustrated, and claimed in this document.

Another alternative to the present invention is use of barcodes. A barcode is machine-readable, using dark ink on a white substrate to create high and low reflectance converted to 1's and 0's representative of information in a visual format on a surface. Barcodes can be read either by optical scanners called barcode readers, or scanned from an image by special software. The use of barcodes, however, in a long-distance wireless communications environment is of questionable practicality.

Accordingly, at least one advantage provided by use of a mobile wireless communications instrument is the capability to electronically and digitally compile information that could be stored in the mobile wireless communications instrument comparable to printed versions of the Physicians' Desk Reference®. The Physicians' Desk Reference ("PDR") is a commercially published compilation of manufacturers' prescribing information on prescription drugs, updated annually. While designed to provide physicians with full, legally mandated information relevant to writing prescriptions, the PDR has become widely available in libraries and bookstores. At least one advantage of an electronic and digital summary of such information would arise from the ability to update information substantially in real time, and to include additional information about medications and treatments of illness as discoveries and/or improvements are developed.

Another advantage provided by use of a mobile wireless communications instrument is the capability of storing on one or more mobile, and/or related mobile or non-mobile communications instruments, including data processors, computers, patient histories and/or patient health records (collectively, in this document, "patient history" or "patient histories"). Such chronological records of significant information relating to a patient's health, treatment, and medication use, and the names and contact information of medication providers, could be updated in substantially real time, and would be available for a review by a medication provider, even for a patient traveling outside the patient's country of residence. In addition, a patient history may also include potentially important information in the form of vital signs. The term "vital signs" as used in this document means at least a patient's pulse rate, respiratory rate, body temperature and ranges, blood pressure, weight, heart rate, and/or blood glucose level, among other vital signs.

There is a worldwide need, therefore, for an apparatus and method that provides and implements a medication management protocol that, in combination with the mobile wireless communications instrument, enables a patient and a medication provider to image-identify and image-authenticate (i) a patient, (ii) a medication provider, (iii) a medication, (iv) correct dosage of a medication for a patient, and (v) correct timing for ingestion or use of a medication by a patient.

A worldwide demand also exists for a system that provides system of medication management that may be used in combination with a mobile wireless communications instrument. As indicated above, mobile wireless communications instruments, including but not limited to mobile cellular telephones, are becoming more and more common worldwide. In addition, many of the mobile wireless communications instruments are equipped with image-making and image transmission features that contribute to implementing the system of medication management. The images may be, for example, in color, black-and-white, for both. Also, the checks and balances provided by the mobile wireless medication management system disclosed, illustrated, and claimed in this document may be transmitted substantially in real time across a wireless communications system to enhance the value of the mobile wireless medication management system.

SUMMARY

The apparatus, system, and method disclosed in this document addresses the above-stated needs by providing a mobile wireless communications instrument. A mobile wireless communications instrument is a useful tool to be used as the primary communications instrument because of the current worldwide growth in use of such instruments, which include cellular telephones and similar instruments used to communicate person-to-person, person-to-object, and object-to-object. A computer, or data processor, or data processing system, is operatively connected to the mobile wireless communications instrument. In one aspect, the data processing system is capable of storing and displaying the steps in a protocol. In another aspect, the data processing system includes a plurality of programmable sets of instruction in a data processor and/or data processor operatively connectable to the mobile wireless communications instrument that includes a medication management protocol executable by the data processing system. The programmable medication management protocol, in combination with the mobile wireless communications instrument, enables a patient and a medication provider to image-identify and image-authenticate the patient, the medication provider, the medication, correct dosage, and correct timing for ingestion or use of a medication. A notification subsystem is included to either confirm or reject use of the medication. The notification subsystem can include an audible, visual, and/or text notification to the patient.

DETAILED DESCRIPTION

Definitions

Figure 1:
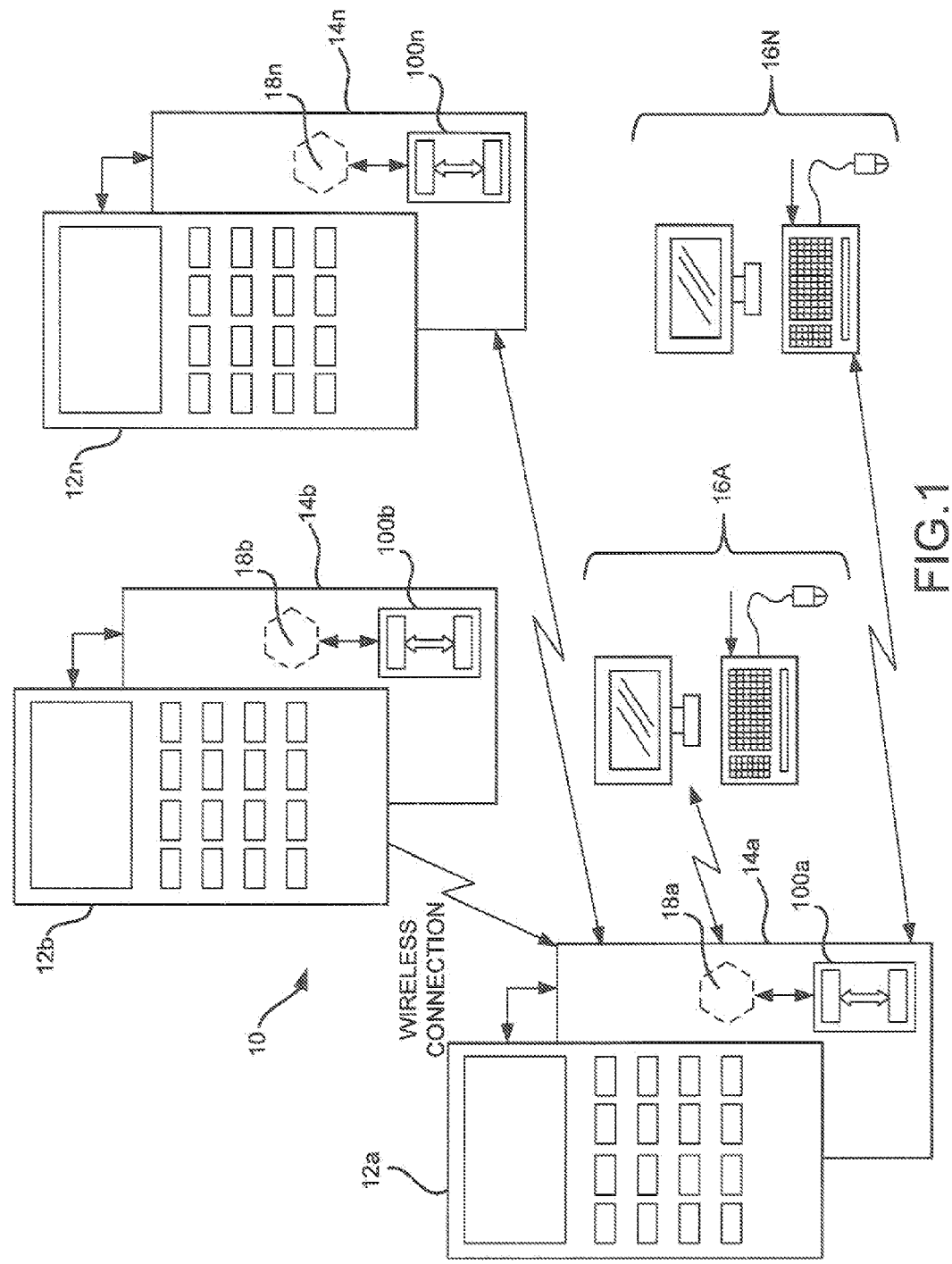
FIG. 1 is a schematic block diagram illustrating the mobile communications instrument and associated data processor or data processing system.

The terms "mobile wireless communication instrument" as used in this document mean at least a wireless communication instrument used in a wireless communications system that, in general, includes an array of operatively connected communication devices adapted to receive and transmit at least electromagnetic signals across the system without cables using infrared light and radio signals, and also includes a telecommunications system in which electromagnetic waves, rather than some form of wire, carry the signal over all or part of the communication path. The mobile wireless communications instrument may also receive and transmit signals from satellites, including satellites that are part of the Global Positioning System (GPS), Galileo, GLONASS, NAVSTAR, GNSS, a system that uses satellites from a combination of these systems, or any Satellite Positioning System (SPS) subsequently developed (collectively referred to generally in this document as a "Satellite Positioning System" (SPS)). As used in this document, an SPS also includes pseudolite (pseudo-satellite) systems.

The term "instrument" in combination with the words "mobile wireless communications," means and includes at least a cellular phone and a pager, a satellite telephone, a two-way pager, a personal digital assistant ("PDA") having wireless capabilities, a portable data processor having wireless capabilities, home entertainment system control boxes, wireless local area networks, and any other type of wireless device having transmission capabilities that may also be one or more versions of a personal communications services device ("PCS") including time division multiple access ("TDMA"), a code division multiple access ("CDMA"), a global system for mobile ("GSM"), a universal mobile telecommunications system ("UMTS"), a wideband code division multiple access ("W-CDMA"), an evolution-data optimized ("EV-DO"), wireless local area network ("WLAN") devices, wireless personal area network ("WPAN") devices, non-voice communications apparatus, and text transmission apparatus, among others. The instrument is preferably equipped with image-making and image transmission features.

The term "medication management protocol" means a procedure for comparing and collating images and related data that enables a patient and a medication provider to image-identify and image-authenticate the patient, the medication provider, the medication, correct dosage, and correct timing for ingestion or use of a medication. The protocol and/or procedure includes a combination of at least a visual image of the patient, a visual image of the container or vial in which medicine is dispenses to the patient, a visual image of a label disclosing the associated medicine and other useful or required information about the medicine, optionally a visual image of at least one sample of the medication, and/or optionally a visual image of a medication provider. The visual images are coordinated with instructions for a step-by-step procedure for achieving the goals of the medical management system. The protocol may be included in a computer processor and/or data processor that present at least visual images and other parameters in the medication management protocol or program, and may present them as step-by-step requirements as conditions or predicates to using and/or ingesting a medicine.

The term "medication provider" means any person authorized to prescribe and/or dispense a medicine, as well as any person authorized to confirm compliance with the protocol described in this document.

The term "image-identify" and/or "image identifications" means to use images that may be obtained and transmitted across a wireless communications system to identify a patient at least by facial recognition, optionally a medication provider at least by facial recognition, a medication, a label for a medication disclosing at least the medicine and other useful or required information, and/or a container for the medication. The term "image-identify" and/or "image identifications" therefore includes the capability of the instrument to capture, store and transmit bionic and/or biometric features of a person, including, but not limited to, iris recognition data, for identification and/or authentication.

The term "container" as used in this document means not only a receptacle for medication, but also an appliance for storing and decanting a medication. One non-exclusive example of an appliance for storing and decanting a medication is vaporizer that provides medicine for a patient to inhale.

The term "image-authenticate" and or "image authentications" means to use images that may be obtained and transmitted across a wireless communications system to confirm that the patient is the correct patient associated with the medication to be used. In addition to photographs of a patient, identification symbols, including biometric derived artifacts used to identify a patient may be included in a photograph. Likewise, the medical history of a patient may be included in the image-authentication.

The term "patient" means any person who is under medical care or treatment who requires use, ingestion, and/or injection of a medication.

The terms "protocol" and/or "procedure" means a way of accomplishing the goal of insuring that a patient uses the correct medication. The protocol and/or procedure includes a combination of at least a visual image of the patient, a visual image the container or vial in which medicine is dispenses to the patient, and optionally a visual image of at least one sample of the medication. The visual images are coordinated with instructions included in a data processor.

The word "exemplary" is used herein to mean "serving as an example, instance, or illustration." Any aspect described in this document as "exemplary" is not necessarily to be construed as preferred or advantageous over other aspects.

DESCRIPTION

The apparatus, system, and method disclosed in this document addresses the above stated needs by providing a mobile wireless communications instrument. A computer and/or data processing system is operatively connected to the mobile wireless communications instrument. The data processing system includes a plurality of user programmable sets of instruction executable by the data processing system for enabling a patient and a medication provider to image-identify and image-authenticate the patient, the medication provider, a medication, a correct dosage of the medication, and correct timing for ingestion or use of the medication, and to either confirm or reject use of the medication by the patient.

Figure 2:
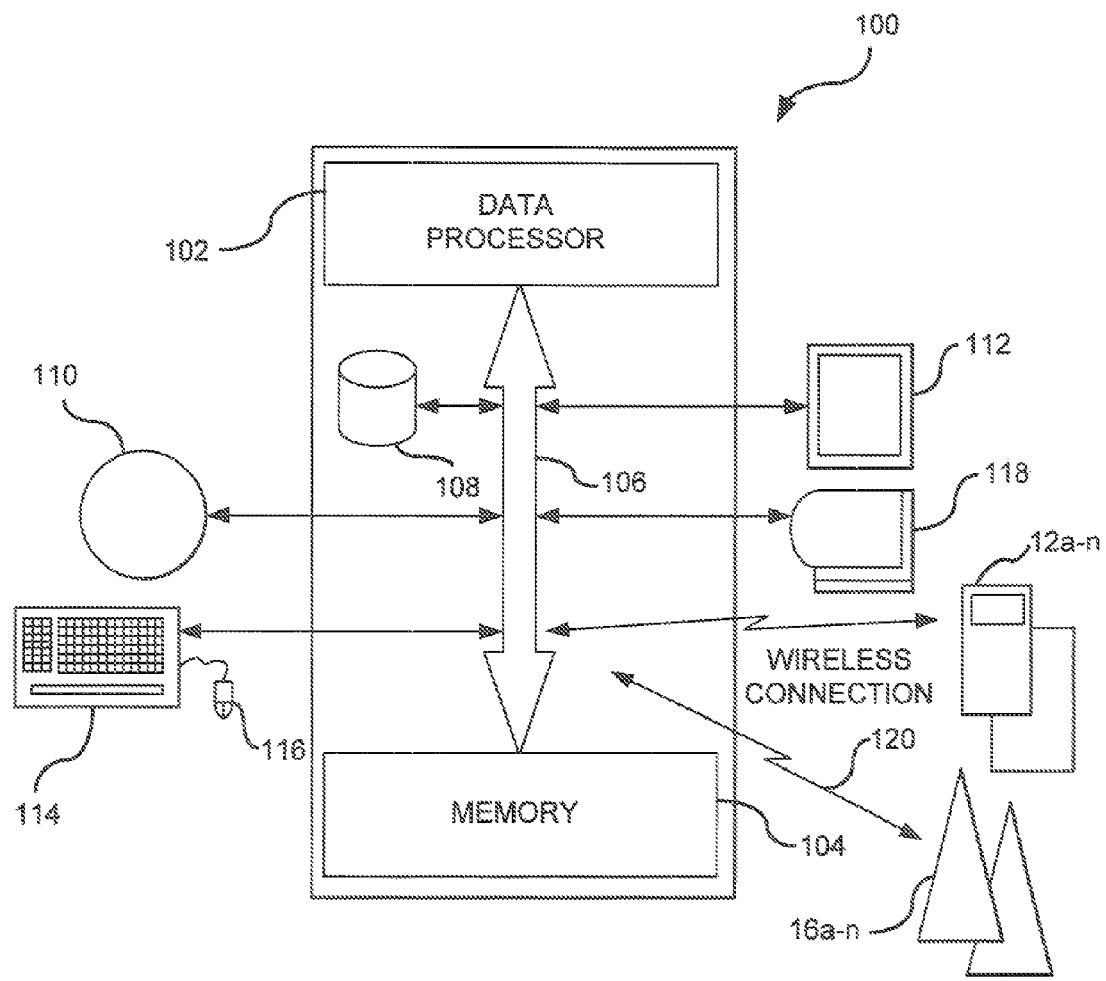
FIG. 2 is a schematic block diagram illustrating the data processor.

More specifically, as illustrated by cross-reference in FIGS. 1-2, in at least one aspect of the apparatus, system, and method disclosed, illustrated and claimed in this document, a medication management system 10 is provided that includes a mobile wireless communications instrument 12a. The mobile wireless communications instrument 12a may be selected from the group of mobile wireless communications instruments consisting of cellular phones; communication apparatus providing personal communications services (PCS) including time division multiple access (TDMA), code division multiple access (CDMA) and global system for mobile (GSM); non-voice communication apparatus; text transmission apparatus; satellite telephones; two-way pagers; personal digital assistants; portable wireless data processors; and a wireless instrument specifically designed for medication management, among others.

As also illustrated in FIGS. 1-2, the medication management system 10 includes a computer, a data processor, and/or data processor (collectively in this document, "data processor"). Data processor 14a is operatively connected to the mobile wireless communications instrument 12a. Data processor 14a also is operatively connectable to one or more mobile wireless communications instruments 12b-n, and also may be operatively connected to one or more non-wireless communications instruments 16a-n that may be neither mobile nor wireless, that may include one or more data processors 14b-n. The one or more non-wireless communications instruments 16a-n that may be neither mobile nor wireless also may be a container, such as a storage and/or decanter container, as described in this document. Accordingly, mobile wireless communications instrument 12a-n is capable of providing images for image identification and for image authentication between and among mobile wireless communications instruments 12a-n and one or more non-wireless communications instruments 16a-n in accordance with a protocol that may be stored in memory of the data processor 14a-n illustrated in block diagram format in FIG. 2.

As illustrated in FIG. 2, the mobile wireless communications instruments 12a-n includes a data processing system 100 as illustrated in a non-exclusive example in the block diagram in FIG. 2. As shown, the data processing system 100 may include a variety of components to enable the mobile wireless communications instruments 12a-n to send and receive data and information, including image identification and image authentication, for use in the medication management system 10. As illustrated, the data processing system 100 includes a data processor 102 and memory 104. A bus 106 connects the data processor 102 and memory 104. Memory 104 is a relatively high-speed machine-readable medium and may include volatile memories such as DRAM, and SRAM, as well as non-volatile memories such as ROM, FLASH, EPROM, EEPROM, and bubble memory. Also connectable to the bus 106 are optional secondary storage 108, external storage 110, output devices such as a monitor 112 that may be operatively connected to the mobile wireless communications instrument 12*a-n*, and in optional configurations an input device such as a keyboard 114 with a mouse 116, and perhaps a printer 118. The optional secondary storage 108 may include machine-readable media such as a hard disk drive, a magnetic drum, and bubble memory. External storage 110 may include machine-readable media such as a floppy disk, a removable hard drive, a magnetic tape, CS-ROM and even other data processors, possibly connected via a communications line 120 to one or more non-wireless communications instruments 16*a-n* as illustrated by cross-reference to FIG. 1.

The distinction between optional secondary storage 108 and external storage 110 is primarily for convenience in describing the invention. As such, a person skilled in the art will appreciate that there is substantial functional overlap between and among the components. Data processor software and user programs can be stored in a software storage medium such as memory 104, optional secondary storage 108, and external storage 110. Executable versions of data processor software can be read from a storage medium such as non-volatile memory, loaded for execution directly into volatile memory, executed directly out of non-volatile memory, or stored in the optional secondary storage 108 prior to leading into volatile memory for execution.

In addition, those skilled in the art also will appreciate that the various illustrative logical blocks, modules, circuits, and algorithm steps described in this document may be implemented as electronic hardware, data processor software, or combination of both. To clearly illustrate this interchangeability of hardware and software, various illustrative and non-exclusive components, blocks, modules, circuits, and steps have been described in this document generally in terms of their functionality. Whether such functionality is implemented as hardware or software depends on the particular application and design constraints imposed on an overall system. Skilled artisans may implement the described functionality in varying ways for each particular application, but such implementation decisions should not be interpreted as causing a departure from the scope of the present invention.

Likewise, the various illustrative logical blocks, modules, and circuits described in connection with the system for medication management disclosed in this document may be implemented or performed with a general purpose data processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof, designed to perform the functions described in this document. A general-purpose processor may be a microprocessor, but in the alternative, the processor may be a conventional processor, controller, microcontroller, or state machine. A processor may also be implemented as a combination of computing devices such as, in a non-exclusive example, a combination of a DSP and a microprocessor, a plurality of microprocessors, one or more microprocessors in conjunction with a DSP core, or any other such configuration.

The medication management system 10 illustrated in FIGS. 1-2 also includes at least one algorithm 18 shown diagrammatically in FIG. 1. The at least one algorithm 18 may be included in the data processing system 100. In one aspect, the at least one algorithm 18 is formulated to be responsive to a protocol for enabling a patient and a medication provider to image-identify and image-authenticate the patient, the medication provider, a medication, a correct dosage of the medication, and correct timing for ingestion or use of the medication, and to either confirm or reject use of the medication by the patient. The images that may be made of the patient, of the medication provider, if desired, of a medication, and of a container of medication, and any other desirable and prudent parameters and data, including vital signs and patient histories, for example, may be associated with the protocol and stored in the mobile wireless communications instrument 12*a*, are transmittable in substantially real time between mobile wireless communications instrument 12*a-n* in the possession of a patient and a medication provider. As part of the protocol to confirm correct dosage of the medication, at the correct time, the images are sent by a patient to a medication provider, and from the medication provider to the patient, before the patient ingests or uses the medication. The medication is not ingested or used by the patient unless and until the patient receives confirmation of ingestion or use of the medication by the patient.

The images may be viewed by the patient on the mobile wireless communications instrument 12*a* or on a non-mobile and/or one or more non-wireless communications instruments 16*a-n*, and by the medication provider either on one or more mobile wireless communications instruments 12*b-n*, or on a non-mobile and/or non-wireless communications instrument 16*b-n*.

Either or both the patient and the medication provider may communicate with one another using the medication management system 10 not only for image-identification and image-authentication, but also audibly and aurally, and by use of text transmissions, to add prudent additional safety steps to ensure compliance with the protocol, a feature that may be particularly useful if the patient has eyesight limitations.

Thus, as one non-exclusive example, the mobile wireless communications instrument 12*a* in the possession of a patient may include a range of selectable options and/or settings that assist either the patient alone, or both the patient and medication provider, that the correct medication, in the correct dosage, is about to be used at the correct time.

Those of skill in the art also will appreciate that the method steps claimed in this document can be interchanged and are interchangeable without departing from the scope of the invention.

Those of skill in the art also would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The previous description of the disclosed aspects is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the aspects shown in this document, but is to be accorded the widest scope consistent with the principles and novel features disclosed herein.

What is claimed is:

1. A system for medication management, comprising:
a mobile wireless communications instrument;
a data processor housed in the mobile wireless communications instrument adapted to receive, store, and transmit images and data;
a programmable medication management protocol stored in the data processor adapted to image-identify and image-authenticate components of the programmable medication management protocol, wherein the programmable medication management protocol is programmed for comparing and collating images and data that enables a patient and a medication provider to:
  image-identify and image-authenticate the patient by facial recognition and/or iris recognition,
  image-identify and image-authenticate the medication provider by facial recognition and/or iris recognition,
  image-identify and image-authenticate a medication by visual image,
  image-identify and image-authenticate correct dosage of the medication by visual image, and
  image-identify and image-authenticate correct timing for ingestion or use of the medication by visual image; and
a notification subsystem configured to allow the medication provider to either confirm or reject use of the medication by the patient.

2. A system for medication management as recited in claim 1, wherein the mobile wireless communications instrument is selected from the group of mobile wireless communications instruments consisting of cellular telephones, communications apparatus providing personal communications services (PCS) including time division multiple access (TDMA), code division multiple access (CDMA) and global system for mobile (GSM), a universal mobile telecommunications system (UMTS), a wideband code division multiple access (W-CDMA), an evolution-data optimized (EV-DO), wireless local area network (WLAN) devices, wireless personal area network (WPAN) devices, non-voice communication apparatus, text transmission apparatus, satellite telephones, two-way pagers, personal digital assistants, portable wireless data processors, and wireless instruments specifically designed to implement medical management transactions.

3. A system for medication management as recited in claim 1, wherein the data processor includes memory.

4. A system for medication management as recited in claim 3, wherein the memory is operatively connected to the data processor by a bus adapted to store at least the programmable medication management protocol executable by the data processor.

5. A system for medication management as recited in claim 1, wherein the data processor further comprises at least one algorithm responsive to the programmable medication management protocol.

6. A system for medication management as recited in claim 1, wherein the components of the programmable medication management protocol include a captured, stored, and cataloged image of a patient's face and/or selected bionic and/or biometric features.

7. A system for medication management as recited in claim 1, wherein the components of the programmable medication management protocol include a captured, stored, and cataloged image of a medication container.

8. A system for medication management as recited in claim 7, wherein the medication container includes a storage and/or decanting appliance.

9. A system for medication management as recited in claim 1, wherein the components of the programmable medication management protocol include a captured, stored, and cataloged image of at least one sample of a solid medication.

10. A system for medication management as recited in claim 1, wherein the components of the programmable medication management protocol include a captured, stored, and cataloged image of at least one sample of a liquid medication vial.

11. A system for medication management as recited in claim 1, wherein the images are in color and/or black-and-white.

12. A system for medication management as recited in claim 1, wherein the notification subsystem includes an audible, visual, and/or text notification to the patient.

* * * * *